(12) United States Patent
Pinchot

(10) Patent No.: US 7,838,856 B2
(45) Date of Patent: *Nov. 23, 2010

(54) COLLIMATOR FABRICATION

(75) Inventor: James M. Pinchot, Parma, OH (US)

(73) Assignee: JMP Industries, Inc., Cleveland, OH (US)

( * ) Notice: Subject to any disclaimer, the term of this patent is extended or adjusted under 35 U.S.C. 154(b) by 271 days.

This patent is subject to a terminal disclaimer.

(21) Appl. No.: 12/265,825

(22) Filed: Nov. 6, 2008

(65) Prior Publication Data

US 2009/0057581 A1 Mar. 5, 2009

Related U.S. Application Data

(60) Division of application No. 11/732,237, filed on Apr. 3, 2007, now Pat. No. 7,462,854, which is a continuation of application No. 11/269,381, filed on Nov. 8, 2005, now abandoned, which is a continuation of application No. 10/687,685, filed on Oct. 17, 2003, now abandoned.

(51) Int. Cl.
*G21F 5/00* (2006.01)
*G01N 23/201* (2006.01)

(52) U.S. Cl. .............. 250/515.1; 250/505.1; 250/506.1; 378/147; 378/149; 204/298.11

(58) Field of Classification Search .............. 250/506.1, 250/505.1, 515.1, 526; 378/84, 147, 149, 378/154, 155; 204/298.11
See application file for complete search history.

(56) References Cited

U.S. PATENT DOCUMENTS

| | | | |
|---|---|---|---|
| 3,701,619 A | 10/1972 | Appeldoorn | |
| 3,881,701 A | 5/1975 | Schoenman et al. | |
| 3,988,589 A | 10/1976 | Leask | |
| 4,450,706 A | 5/1984 | Engelmohr | |
| 4,516,632 A | 5/1985 | Swift et al. | |
| 4,869,421 A * | 9/1989 | Norris et al. | 228/181 |
| 5,031,483 A | 7/1991 | Weaver | |
| 5,071,503 A | 12/1991 | Berman | |
| 5,137,369 A | 8/1992 | Hodan | |
| 5,250,263 A | 10/1993 | Manz | |
| 5,398,193 A | 3/1995 | DeAngelis | |
| 5,514,232 A | 5/1996 | Burns | |
| 5,534,328 A | 7/1996 | Ashmead et al. | |
| 5,544,771 A | 8/1996 | Lee et al. | |
| 5,580,523 A | 12/1996 | Bard | |
| 5,595,712 A | 1/1997 | Harbster et al. | |
| 5,658,537 A | 8/1997 | Dugan | |
| 5,683,828 A | 11/1997 | Spear et al. | |
| 5,690,763 A | 11/1997 | Ashmead et al. | |
| 5,727,618 A | 3/1998 | Mundinger et al. | |

(Continued)

OTHER PUBLICATIONS

U.S. Appl. No. 2002/0048644 published Apr. 25, 2002.

(Continued)

*Primary Examiner*—Bernard E Souw
(74) *Attorney, Agent, or Firm*—Fay Sharpe LLP; Brian E. Turung

(57) ABSTRACT

A collimator that formed from a plurality of metal layers that are shaped by use of lithographic techniques in specific shapes. The formed metal layers are stacked and aligned together and then connected together to form the collimator.

19 Claims, 5 Drawing Sheets

U.S. PATENT DOCUMENTS

| | | | |
|---|---|---|---|
| 5,779,833 A | 7/1998 | Cawley et al. | |
| 5,843,385 A | 12/1998 | Dugan | |
| 5,847,958 A | 12/1998 | Shaikh et al. | |
| 5,872,714 A | 2/1999 | Shaikh et al. | |
| 5,961,932 A | 10/1999 | Ghosh et al. | |
| 5,993,750 A | 11/1999 | Ghosh et al. | |
| 6,048,432 A | 4/2000 | Ecer | |
| 6,075,840 A * | 6/2000 | Pellegrino et al. | 378/154 |
| 6,129,973 A | 10/2000 | Martin et al. | |
| 6,167,910 B1 | 1/2001 | Chow | |
| 6,240,161 B1 | 5/2001 | Siochi | |
| 6,271,524 B1 | 8/2001 | Wainer et al. | |
| 6,287,436 B1 | 9/2001 | Pelletier et al. | |
| 6,324,438 B1 | 11/2001 | Cormier | |
| 6,352,577 B1 | 3/2002 | Martin et al. | |
| 6,377,661 B1 | 4/2002 | Guru et al. | |
| 6,388,816 B2 | 5/2002 | Brown et al. | |
| 6,396,902 B2 | 5/2002 | Tybinkowski et al. | |
| 6,409,072 B1 | 6/2002 | Breuer et al. | |
| 6,484,776 B1 | 11/2002 | Meilunas et al. | |
| 6,490,812 B1 | 12/2002 | Bennett et al. | |
| 6,494,614 B1 | 12/2002 | Bennett et al. | |
| 6,507,642 B2 | 1/2003 | Fujishige et al. | |
| 6,526,123 B2 | 2/2003 | Ein-Gal | |
| 6,527,890 B1 | 3/2003 | Briscoe et al. | |
| 6,533,840 B2 | 3/2003 | Martin et al. | |
| 6,556,657 B1 | 4/2003 | Tybinkowski et al. | |
| 6,561,208 B1 | 5/2003 | O'Connor et al. | |
| 6,575,218 B1 | 6/2003 | Burns et al. | |
| 6,587,742 B2 | 7/2003 | Manuel et al. | |
| 6,592,696 B1 | 7/2003 | Burdon et al. | |
| 6,643,302 B1 | 11/2003 | Nishikawa et al. | |
| 6,645,432 B1 | 11/2003 | Anderson et al. | |
| 6,654,656 B2 | 11/2003 | Kesavadas et al. | |
| 6,672,502 B1 | 1/2004 | Paul et al. | |
| 6,676,835 B2 | 1/2004 | O'Connor et al. | |
| 6,692,700 B2 | 2/2004 | Handique | |
| 6,695,044 B1 | 2/2004 | Symonds | |
| 6,729,352 B2 | 5/2004 | O'Connor et al. | |
| 6,987,836 B2 * | 1/2006 | Tang et al. | 378/154 |
| 7,310,411 B2 * | 12/2007 | Tang et al. | 378/154 |
| 2002/0009741 A1 | 1/2002 | Simpson et al. | |
| 2002/0119079 A1 | 8/2002 | Breuer et al. | |
| 2002/0189530 A1 | 12/2002 | David | |
| 2002/0195048 A1 | 12/2002 | David | |
| 2002/0195052 A1 | 12/2002 | David | |
| 2003/0027022 A1 | 2/2003 | Arana et al. | |
| 2003/0083410 A1 | 5/2003 | Baur et al. | |
| 2003/0152488 A1 | 8/2003 | Tonkovich et al. | |
| 2003/0158410 A1 | 8/2003 | Nickel et al. | |
| 2003/0164118 A1 | 9/2003 | Nickel et al. | |
| 2003/0180216 A1 | 9/2003 | TeGrotenhuis et al. | |
| 2003/0204228 A1 | 10/2003 | Thomas et al. | |
| 2003/0204285 A1 | 10/2003 | Thomas et al. | |
| 2003/0223909 A1 | 12/2003 | Oberbeck et al. | |
| 2003/0235272 A1 | 12/2003 | Appleby et al. | |
| 2005/0084072 A1 * | 4/2005 | Pinchot | 378/154 |
| 2006/0054841 A1 * | 3/2006 | Pinchot | 250/505.1 |

OTHER PUBLICATIONS

U.S. Appl. No. 2002/0106311 published Aug. 8, 2002.
U.S. Appl. No. 2003/0091496 published May 15, 2003.
U.S. Appl. No. 2003/0128812, published Jul. 10, 2003.

* cited by examiner

COLLIMATOR FABRICATION

The present invention is a divisional of U.S. patent application Ser. No. 11/732,237 filed Apr. 3, 2007, now U.S. Pat. No. 7,462,854 which in turn is a continuation of U.S. patent application Ser. No. 11/269,381 filed Nov. 8, 2005, now abandoned which in turn is a continuation of U.S. patent application Ser. No. 10/687,685 filed Oct. 17, 2003, now abandoned.

This invention relates in general to grid-like structures of the type suitable for use as collimators. In particular, the invention relates to a method and an apparatus for forming collimator strips which can be assembled to form a collimator that can be used in imaging, diagnosing and/or treatment apparatuses that take images and/or effect treatment by use of gamma rays, electron beams, photon (X-ray) beams, or similar penetrating rays.

BACKGROUND OF INVENTION

Radiation emitting devices are generally known and used as imaging and as radiation therapy devices for the treatment of patients.

Collimators are used in a wide variety of equipment in which it is desired to permit only beams of radiation emanating along a particular path to pass beyond a selected point or plane. Collimators are frequently used in radiation imagers to ensure that only radiation beams emanating along a direct path from the known radiation source strike the detector, thereby minimizing detection of beams of scattered or secondary radiation. Collimator design affects the field-of-view, spatial resolution, and sensitivity of the imaging system.

Particularly in radiation imagers used for medical diagnostic analyses or for non-destructive evaluation procedures, it is important that only radiation emitted from a known source and passing along a direct path from that source through the subject under examination be detected and processed by the imaging equipment. If the detector is struck by undesired radiation, i.e., radiation passing along non-direct paths to the detector, such as rays that have been scattered or generated in secondary reactions in the object under examination, performance of the imaging system is degraded. Performance is degraded by lessened spatial resolution and lessened contrast resolution that result from the detection of the scattered or secondary radiation rays. Examples of imagers and collimators for such imagers are disclosed in U.S. Pat. Nos. 6,556,657; 6,507,642; 6,505,966; 6,396,902; 6,388,816; 6,377,661; and 6,271,524, all of which are incorporated herein by reference.

Collimators are positioned to substantially absorb the undesired radiation before it reaches the detector. Collimators are traditionally made of a material that has a relatively high atomic number, such as tungsten, placed so that radiation approaching the detector along a path other than one directly from the known radiation source strikes the body of the collimator and is absorbed before being able to strike the detector. In a typical detector system, the collimator includes barriers extending outwardly from the detector surface in the direction of the radiation source so as to form channels through which the radiation must pass in order to strike the detector surface.

Some radiation imaging systems, such as computed tomography (CT) systems used in medical diagnostic work, or such as industrial imaging devices, use a point (i.e. a relatively small, such as 1 mm in diameter or smaller) source of x-ray radiation to illuminate the subject under examination. The radiation passes through the subject and strikes a radiation detector positioned on the side of the subject opposite the radiation source. In a CT system, the radiation detector typically comprises a one-dimensional array of detector elements. Each detector element is disposed on a module, and the modules are typically arranged end to end along a curved surface to form a radiation detector arm. The distance to the center of the module, on any one of the separate modules is the same, i.e., each panel is at substantially the same radius from the radiation source. On any given module there is a difference from one end of the module to the other in the angle of incidence of the radiation beams arriving from the point source.

For example, in a common medical CT device, the detector is made up of a number of x-ray detector modules, each of which has dimensions of about 32 mm by 16 mm, positioned along a curved surface having a radius of about 1 meter from the radiation point source. Each detector module has about 16 separate detector elements about 32 mm long by 1 mm wide arranged in a one-dimensional array, with collimator plates situated between the elements and extending outwardly from the panel to a height above the surface of the panel of about 8 mm. As the conventional CT device uses only a one-dimensional array (i.e., the detector elements are aligned along only one row or axis), the collimator plates need only be placed along one axis, between each adjoining detector element. Even in an arrangement with a panel of sixteen 1 mm-wide detector elements adjoining one another (making the panel about 16 mm across), if the collimator plates extend perpendicularly to the detector surface, there can be significant "shadowing" of the detector element by the collimator plates toward the ends of the detector module. This shadowing results from some of the beams of incident radiation arriving along a path such that they strike the collimator before reaching the detector surface. Even in small arrays as mentioned above (i.e. detector panels about 16 mm across), when the source is about 1 meter from the panel with the panel positioned with respect to the point source so that a ray from the source strikes the middle of the panel at right angles, over 7.5% of the area of the end detector elements is shadowed by collimator plates that extend 8 mm vertically from the detector surface. Even shadowing of this extent can cause significant degradation in imager performance as it results in non-uniformity in the x-ray intensity and spectral distribution across the detector module. In the one-dimensional array, the collimator plates can be adjusted slightly from the vertical to compensate for this variance in the angle of incidence of the radiation from the point source.

Advanced CT technology (e.g., volumetric CT), however, makes use of two-dimensional arrays, i.e., arrays of detector elements that are arranged in rows and columns. The same is true of the precision required for industrial imagers. In such an array, a collimator must separate each detector element along both axes of the array. The radiation vectors from the point source to each detector on the array have different orientations, varying both in magnitude of the angle and direction of offset from the center of the array. Additionally, detector arrays larger than the one-dimensional array discussed above may be advantageously used in imaging applications. As the length of any one panel supporting detector elements increases, the problem of the collimator structure shadowing large areas of the detector surface become more important. In any system using a "point source" of radiation and flat panels, some of the radiation beams that are desired to be detected. i.e., ones emanating directly from the radiation source to the detector surface, strike the detector surface at some angle offset from vertical.

Gamma ray imaging is currently used in medicine to obtain 3D images of patients' internal organs. One such gamma ray imaging device is disclosed in U.S. Pat. No. 6,271,524, which is incorporated herein by reference. Positron Emission Tomography (PET) is a medical gamma ray imaging technique frequently used for this purpose. Prior to conducting the imaging procedure, a patient is given a radio-pharmaceutical, which contains a positron emitting substance and which is selectively accumulated in a region of interest. When a positron emitted by the radio-pharmaceutical encounters an electron, the electron-positron pair annihilates, emitting two gamma photons of 511 keV each, flying in opposite directions. The simultaneous detection of these gamma photons by two gamma detectors positioned opposite to each other, indicates that a positron has been emitted and annihilated inside an organ of a patient. The simultaneous attribution of 2D coordinates to each one of the photons allows for the determination of the photon's line of flight. The position of the annihilation is along this line. When a multitude of gamma photon pairs are detected and the information is processed using appropriate algorithms, electronic circuitry, software, etc., a 3D image of the organ under examination can be reconstructed.

In radiation therapy, the device generally includes a gantry which can be swivelled around a horizontal axis of rotation in the course of a therapeutic treatment. Two such devices are disclosed in U.S. Pat. Nos. 6,526,123 6,240,161, both of which are incorporated herein by reference. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation. To control the radiation emitted toward an object, a beam shielding device, such as a plate arrangement or a collimator, is typically provided in the trajectory of the radiation beam between the radiation source and the object.

A collimator is a beam shielding device which can include multiple leaves, for example, a plurality of relatively thin plates or rods, typically arranged as opposing leaf pairs. The plates themselves are formed of a relatively dense and radiation impervious material and are generally independently positionable to delimit the radiation beam. The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor. Once an analysis is completed as to the intensity level of radiation at a particular region on the body, the beam shielding device settings must be chosen according to the output number of fields. Often, the application of a particular sequence of radiation requires a prohibitive amount of time to deliver, or which is physically impossible for the beam shielding device to achieve. As a result, to provide a realizable dosage, fewer intensity levels of radiation must be provided, and/or fewer radiation fields are used, thus the dose volume histograms are thereby degraded. While methods are known to address deliver dosage demands according to the intensity maps (See U.S. Pat. No. 5,663,999), such systems still cause a degradation of the dose volume histogram.

Various methods have been used to manufacture thicker collimators. One method is to cast the collimator. Several methods of casting are disclosed in U.S. Pat. No. 3,988,589, which is incorporated herein by reference. One casting method is to cast the collimator as a single unit using removable pins in the mold to provide holes in the collimator. This method of manufacture, while producing an operational collimator, is impractical since, due to high friction between the cast lead and the pins and the fact that some collimators are convergent or divergent (to allow enlarged or miniaturized image formation) relative to the radiation source, each of the pins used to create the holes must be removed individually. This process is time consuming and costly, especially when one realizes that some such collimators have 1000 or more such holes. Another casting method is to cast thick corrugated lead sheets and assemble them. This alternative also is unsatisfactory due to joint leakage (i.e. the epoxied joints are permeable to high energy radiation) and to too much distorting radiation reaching the receiver of the medical device. Still another casting method is to cast a plurality of modules that are press fitted or cemented together to form the collimator.

Several other methods for forming collimators are disclosed in U.S. Pat. No. 4,450,706, which is incorporated herein by reference. One method includes the dissolving metal by a chemical reagent to form a specific collimator shape. Another method includes wrapping radiation-absorbing foils around a large number of mandrels. Another method involves the formation of a plurality of collimator strips which are folded transversely to their longitudinal extension such that the flat portions of two adjacent strips engage each other, whereby the outwardly extending portions of these two adjacent strips extend in opposite directions to form a series of parallel channels. Still another method involves the use of strips that have been stamped into a shape and subsequently bonded together.

The casting methods described above for manufacturing a collimator can only be used to fabricate relatively simple collimators having high error tolerances in design. As technology has advanced, a need for more complex collimators has arisen wherein such collimators have very low error tolerances. One manufacturing method to address this problem is disclosed in U.S. Pat. No. 6,377,661, which is incorporated herein by reference. This patent discloses a collimator manufacturing process which includes the steps of generating a computer-aided-drawing (AutoCAD) drawing of a two-dimensional (2D) collimator based upon overall imager system parameters, generating a stereo-lithographic (STL) file or files corresponding to the AutoCAD drawing and to the chosen size, position and orientation of the focally aligned channels to be formed in the collimator, and interfacing the STL files with machining equipment to machine out the material to be removed from a solid slab (workpiece) of radiation-absorbing material, to form the plurality of focally aligned channels extending through the workpiece.

Another method for manufacturing a collimator is disclosed in United States Patent Publication No. 2003/0128813 published on Jul. 10, 2003 entitled "Devices, methods, and systems involving cast computed tomography collimators" and 2003/0128812 published on Jul. 10, 2003 entitled "Devices, methods, and systems involving cast collimators", both of which are incorporated herein by reference. In this patent publication, a cast computed-tomography collimator is formed from a litho graphically-derived micro-machined metallic foil stack lamination mold. The mold has a stacked plurality of micro-machined metallic foil layers. The mold is filled with a first casting material to form a collimator.

Although these casting techniques have improved the quality of collimator production, the casting process still cannot meet certain tolerances that are needed for highly sensitive medical devices. In view of the prior art, there is a need for a manufacturing process for a collimator that is cost effective, not overly time consuming to manufacture, and which can produce a very precise collimator in a variety of shapes and sizes.

SUMMARY OF THE INVENTION

The present invention pertains to a method for manufacturing a collimator for use in medical devices and will be described with particular reference thereto; however, the invention has much broader applications and can be used to form a collimator for applications in devices other than medical devices. In additional, the invention can be expanded beyond collimators and can be used to form a variety of metallic and non-metallic materials that require very low error tolerances. The novel method of manufacturing the collimator includes 1) generating a computer image of the collimator, 2) sectioning the computer generated image, 3) forming sections of the collimator from a metal material based on each of the drawing sections, and 4) connecting the individual sections to form a collimator that substantially matches the computer generated drawing of the collimator. By using this novel manufacturing technique, collimators having very precise dimensions can be manufactured having very low error tolerances.

In one aspect of the invention, the computer drawing of the collimator can be generated by commercially available or proprietary software. One common commercial software package is AutoCAD. Many other software packages can be used. The computer drawing is at least a two dimensional drawing and typically a three dimensional drawing of the collimator. Once the computer generated drawing matches the shape of the collimator, the drawing is then sectioned to emulate layers of the collimator. Typically, the layers are divided or sectioned along the longitudinal axis or vertical axis of the collimator; however, layers of the collimator can be divided along other axes of the collimator. The divided or sectioned layers typically have the same thickness, however, this is not required. The computer generated images for the collimator can be saved, used in other processes (e.g., lithography process, etc.) or the like.

In still another and/or alternative embodiment of the invention, one or more sections of the collimator are formed from a metal material that matches low error tolerances. Various techniques can be used to produce the one or more sections of the collimator. In one embodiment of the invention, lithography is used to at least partially form one or more sections of the collimator. When using a lithography process, a photo-sensitive resist material coating is applied to one or more of the surfaces (i.e., either of the relatively large planar "top" or "bottom" surfaces) of a blank of metal material (e.g. metal foil, etc.). After the blank has been provided with the photo-resist material coating, "mask tools" or "negatives" or "negative masks", containing a positive or negative image of the desired section of the collimator are etched in the blank. The mask tools can be made from glass or other materials, which has a relatively low thermal expansion coefficient and transmits radiation such as ultraviolet light. The blank is then exposed to radiation, typically in the form of ultraviolet light, to expose the photo-resist coatings to the radiation. The masks are then removed and a developer solution is applied to the surfaces of the blank to develop the exposed (sensitized) photo-resist material. Once the photo-resist is developed, the blanks are etched or micro-machined. Once etching or machining is complete, the remaining unsensitized photo-resist material can be removed such as by, but not limited to, a chemical stripping solution. When using lithography as a basis for layer fabrication of the collimator sections, parts and/or features can be designed as diameters, squares, rectangles, hexagons, and/or any other shape and/or combination of shapes. The combinations of any number of shapes can result in non-redundant design arrays (i.e. patterns in which not all shapes, sizes, and/or spacings are identical). Lithographic features can represent solid or through aspects of the final collimator. Such feature designs can be useful for fabricating micro-structures, surfaces, and/or any other structure that can employ a redundant and/or non-redundant design for certain micro-structural aspects. Large area, dense arrays can be produced through the lithographic process, thereby enabling creation of devices with sub-features or the production of multiple devices in a batch format. Lithography can also allow the creation of very accurate feature tolerances since those features can be derived from a potentially high-resolution photographic mask. The tolerance accuracy can include line-width resolution and/or positional accuracy of the plotted features over the desired area. Photographic masks can assist with achieving high accuracy when chemical or ion-etched, or deposition-processed layers are being used to form a collimator from the stack of sections. Because dimensional changes can occur during the final formation of the collimator, compensation factors can be engineered at the photo-mask stage, which can be transferred into the fabrication of the collimator. For instance, when the full collimator or a portion of the collimator needs to be angled for radial designs or other designs, the photo-mask typically needs to be applied to both sides of the metal foil layer with a slight offset to allow for the angle. This offset will eliminate a stack-up look even though the steps will be very thin. When the brazing material is coated on both sides of every other metal foil layer, the etching solution typically performs a better job to form a better angled stack. In another and/or alternative embodiment, fabricating the sections of the collimator can be formed by one or more micro-machining techniques. Some of the micromachining techniques that can be used include, but are not limited to, photo-etching, laser machining, reactive ion etching, electroplating, vapor deposition, bulk micro-machining, surface micro-machining, and/or conventional machining. Ion etching techniques can form sections of the collimator that have tolerances of less than about 1.25 microns. Photochemical-machining techniques can etched a section of the collimator to tolerances of less than about 2.5 microns or about 10% of the metal thickness. Laser micro-machining techniques can produce sections of the collimator to a tolerance of less than about 0.3 micron. Electro-forming techniques can produce sections of the collimator to a tolerance of less than about 0.1 micron.

In yet another and/or alternative embodiment of the invention, one or more sections of the collimator are connected together by a lamination process. Once the multiple sections of the collimator are formed in the metal material, the sections are placed together to define the desired collimator. The total number (and thickness) of the collimator sections define the overall height and aspect ratio of the collimator. In one embodiment, a metal-to-metal brazing technique is used to connect together one or more sections of the collimator. Prior to the assembly of the collimator, one or more sections of the collimator can have one or both surfaces coated with a thin metal layer. In one non-limiting example, the metal foil layers are coated on one side of each foil layer. In another non-limiting example, the both sides of "every other" metal foil layer are coated with the brazing metal. Such coating techniques can include, but are not limited to, thermal spraying and electroplating. Generally the thickness of the metal coating is less than about 10 microns and typically about 0.1-10 microns, and more typically about 0.5-4 microns. The coated metal should have a relatively high density (e.g. 8.5 g/cm³ or greater) and a melting temperature that is less than the metal used to form the sections of the collimator. Typically the average density of the coating metal is at least about 8.8 g/cm³ and has an average metaling point that is at least about 10° C. less than the average melting point of the metal used to form the sections of the collimator, and typically is at least about 500° C. less than the average melting point of the metal used to form the sections of the collimator. Examples of coating metal materials include, but are not limited to, copper, gold, lead, nickel, platinum and silver. As can be appreciated, alloys of these metals and/or other high density metals can be used. During the brazing process, the sectioned assembly can be heated in an inert atmosphere to an elevated temperature to cause the metal coating to flow. The heating of the brazing metal can be achieved by use of induction heating, radiant heating, lasers, furnaces, ovens, etc. Typically the brazing temperature is at least about 10° C. higher than the average melting point of the brazing metal and at least 100° C. less than the average melting point of the metal foil. The atmosphere about the collimator sections can be held under vacuum to result in a vacuum brazing process. The atmosphere is typically an inert atmosphere. Gas atmospheres that include hydrogen, nitrogen or noble gases can be used. The time of brazing is typically about 0.1-4 hours. The elevated temperature during brazing causes the brazing metal to flow between the metal foil layers. The brazing procedure is completed by cooling the layered collimator. The atmosphere during cooling is typically inert. The cooling times are typically 0.1-5 hours. As the temperatures elevate, the sections of the collimator can expand. Various types of alignment structures (e.g., pins, etc.) can be used to maintain the sections of the collimator in the proper position during the heating process. In one non-limiting embodiment, construction holes or slots are formed in each foil layer which are used to align the foil layers. The construction holes or slots can be sized and shaped to account for expansion and/or contraction of the foil layers when exposed to heat. Typically, each foil layer includes a plurality of construction holes or slots to facilitate in the proper orientation of the layer layers when forming the collimator. The pins can be made of the same or similar expanding and contracting material as the foil layers so that the pins expand and contact at the same rate as the foil layers when exposed to heating and cooling. As such, the brazing fixtures (e.g., pins) typically are made of a material that has a coefficient of linear expansion close to that of the metal leaves so that the fixtures grow in the furnace at substantially the same rate as the collimator assembly grows and shrinks at substantially the same rate when the collimator is cooled. Alternatively, the pins can be formed of carbon material (e.g. graphite) or other type of material that has little or no expansion during heating and cooling. The carbon material has a very low expansion rate and can take the heat during the brazing process. The difference in expansion rates using carbon pins can be easily incorporated in the design of the slots in the metal foil layers. In addition, the carbon pins are less apt to "stick" to any brazing material that may seep from the stacked metal foil layers thus improving the quality of the final formed product. The layers of metal foil can also be clamped together or otherwise placed under pressure to limit movement of the foil layers during the brazing process. In addition to using alignment structures, positional errors of the collimator sections (stacking errors) and tolerances can be controlled by the photographic masks used to produce the layers. The geometric size and tolerance of the sections can be partially controlled by the layer thickness and/or microma-chining methods used to produce the sections. When producing a laminated collimator, numerous factors can be an influence on the overall tolerances of the sections of the collimator. For example, when using a stacking fixture, the flatness of the laminating surface of the collimator sections and the perpendicularity of the sides of the collimator sections can be controlled. In addition, the dimensional tolerance of the alignment features of a collimator section and/or the positional tolerance of a collimator section can be an influence. In another and/or alternative embodiment of the invention, one or more layers of metal foil can be laminated together by use of an adhesive. Such adhesives can include, but are not limited to, thermo-cured epoxy, non-thermo-cured epoxy, silicone rubber products, urethanes, etc. When using lamination techniques other than brazing, the layers of the collimator are typically clamped together or otherwise placed under pressure until the adhesive has at least partially dried and/or cured.

In still yet another and/or alternative embodiment of the invention, the metal sections of the collimator are formed from high density metal foil. The metal foil can be made of a single metal or be a metal alloy. The average density of the metal forming the metal foil is greater than about 8.5 g/cm³, and typically greater than about 9 g/cm³. In addition, the average melting point of the metal forming the metal foil is generally greater than about 100° C., and typically greater than about 1500° C. The metal forming the metal foil is also non-radioactive or substantially non-radioactive (i.e. stable). Non-limiting examples of the metals that can be used individually or in combination with other metals to form the metal foil include bismuth, cadmium, cobalt, copper, erbium, gold, hafnium, iridium, lead, nickel, niobium, osmium, palladium, platinum, rhenium, rhodium, ruthenium, silver, tantalum, technetium, terbium, thallium, thulium and/or tungsten. The metal foil is selected to have a thin thickness. The thin thickness facilitates in the ease of processing the metal foil during the lithography process and also results in a higher quality final product. Generally the foil thickness is about 10-400 microns, and more typically about 40-150 microns.

A primary object of the present invention is a manufacturing process for a collimator that forms the collimator with high precision.

Another and/or alternative object of the present invention is a manufacturing process for a collimator that includes the use of computer generated images and lithographic techniques to manufacture a manufacturing process for a collimator.

Still another and/or alternative object of the present invention is a manufacturing process for a collimator that includes the connecting of thin layers of dense metal to form the collimator.

Yet another and/or alternative object of the present invention is a manufacturing process for a collimator that includes vacuum brazing to connect together one or more layers of a collimator.

Still yet another and/or alternative object of the present invention is a manufacturing process for a collimator that includes a lithographic technique to form distinct shapes in a metal foil that is representative of a section of the collimator.

A further and/or alternative object of the present invention is a manufacturing process for a collimator that utilizes guide structures and holes or slots to properly align the foil layers to facilitate in the proper formation of the collimator.

Still a further and/or alternative object of the present invention is a manufacturing process for a collimator that includes coating one or more sides of a metal foil with a thin metal layer for use in brazing one or more metal foil layers together to form a collimator.

Yet a further and/or alternative object of the present invention is a manufacturing process for a collimator that can form a collimator having a planar shape, a curvilinear shape or any other desired simple or complex shape.

Still yet a further and/or alternative object of the present invention is a manufacturing process for a collimator that can form a collimator having a simple or complex face surface.

These and other objects and advantages will become apparent from the discussion of the distinction between the invention and the prior art and when considering the preferred embodiment as shown in the accompanying drawings.

BRIEF DESCRIPTION OF THE DRAWINGS

The foregoing objects, and others, will in part be obvious and in part pointed out more fully hereinafter in conjunction with the written description of preferred embodiments of the invention illustrated in the accompanying drawings in which.

DETAILED DESCRIPTION OF ONE PREFERRED EMBODIMENT

Figure 1:
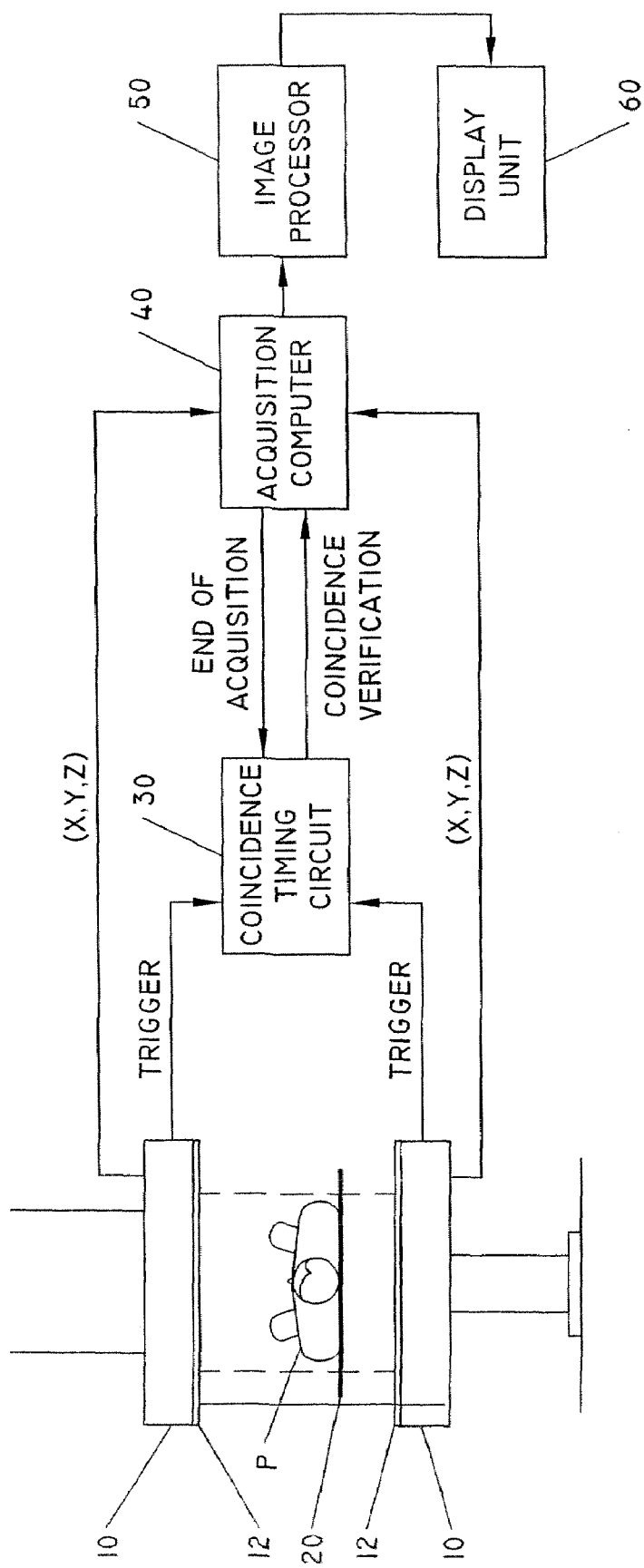
FIG. 1 is a general block diagram of a prior art gamma ray imaging device that can be used with the collimator of the present invention.

Referring now in greater detail to the drawings, wherein the showings are for the purpose of illustrating preferred embodiments of the invention only and not for the purpose of limiting the invention, FIG. 1 shows a block diagram of a prior art gamma ray detector system used for diagnostic purposes. A pair of gamma detectors 10, each optically coupled to a scintillation crystal 12, are disposed parallel to each other. Detector pair 10 is mounted on a gantry that can rotate about a patient P resting on a table 20. Additionally, either detector pair 10 or patient P can be transversely displaced in the direction perpendicular to the plane of the figure. This configuration allows for total body scanning and/or static imaging both well-known techniques in NM coincidence measurements.

System hardware and software, schematically described in FIG. 1 by blocks 30, 40, 50 and 60, allows for coincidence measurements in accordance with technology well known in the art. Thus, no further details on system operation will be given in the description of preferred embodiments in accordance with the present invention, except for distinctive features of the invention. This hardware generally includes an energy discriminator that rejects events having a low energy. Such events are presumed to be caused by scatter.

Prior to an imaging procedure, patient P is given a radiopharmaceutical, which contains a positron emitting substance and which is selectively accumulated in a region of interest. When a positron emitted by the radiopharmaceutical encounters an electron, the electron-positron pair annihilates, emitting two gamma photons of 511 keV each, flying in opposite directions. The simultaneous detection of these two 511 keV gamma photons by the two gamma detectors 10 positioned opposite to each other, indicates that a positron has been emitted and annihilated inside an organ of a patient P. The simultaneous attribution of 2D coordinates to each one of the photons allows for the determination of the photon's line of flight. The position of the annihilation is along this line. When a multitude of gamma photon pairs are detected and the information processed using appropriate algorithms, electronic circuitry, software, etc., a 3D image of the organ under examination is reconstructed. A collimator is used to detect gamma photons along a particular path. The detected gamma photos are then used to image a particular portion of the patient's body for diagnostic purposes. It is desirable, in PET, to improve the efficiency of gamma detectors by reducing the number of stray photons detected relative to the number of non-stray photons detected and to improve the depth discrimination in coincidence measurements. It is also desirable to perform attenuation and coincidence measurements in sequence without moving or replacing parts of the imaging system and, in attenuation measurements, to reduce radioactivity losses due to line source diameter while using a large diameter source to improve statistics by increasing the total radiation while keeping the source strictly collimated. To achieve these results, collimators having specific designs are used.

Figure 2:
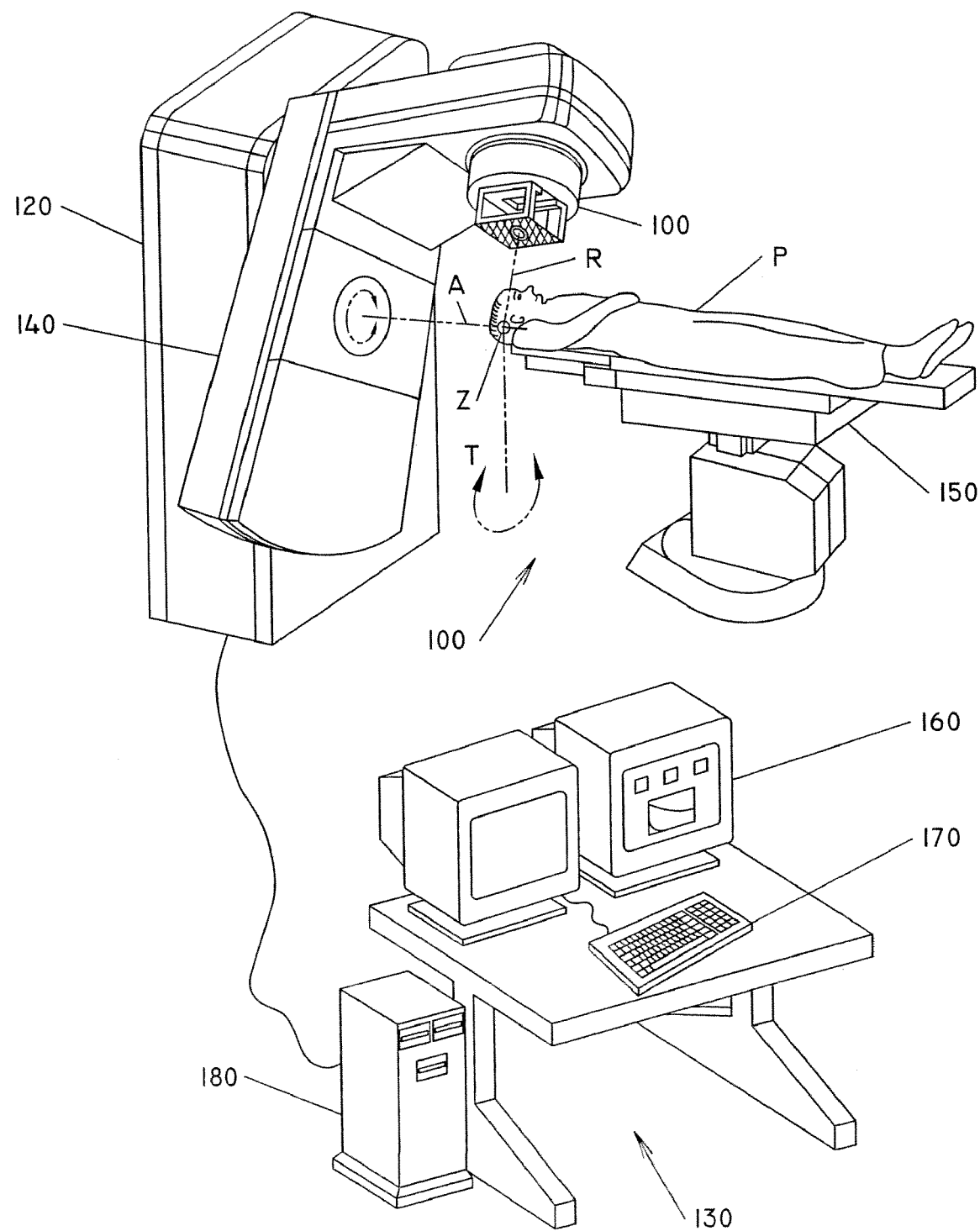
FIG. 2 is a general diagram of a radiation treatment device and treatment console that can be used with the collimator of the present invention.

Referring now to FIG. 2, there is illustrated a prior art radiation treatment apparatus 100. The radiation treatment apparatus 100 includes a beam shielding device (not shown) within a treatment head 110, a control unit in a housing 120 and a treatment unit 130. The radiation treatment device 110 includes a gantry 140 which can be swivelled around a horizontal axis of rotation A in the course of a therapeutic treatment. The treatment head 110 is fastened to projection of the gantry 140. A linear accelerator is located in the gantry 140 to generate the high powered radiation required for the therapy. The axis of the radiation bundle emitted from the linear accelerator and the gantry 140 is designated by R. Electron, photon or any other detectable radiation can be used for the therapy. During the treatment, the radiation beam is trained on a zone Z on a patient P who is to be treated and who lies at the isocenter of the gantry rotation. The rotational axis A of the gantry 110, the rotational axis T of a treatment table 150, and the beam axis R intersect in the isocenter. The plates or leaves of the beam shielding device within the treatment head 110 are substantially impervious to the emitted radiation. The collimator is mounted between the radiation source and the patient in order to delimit the field. Areas of the body, for example, healthy tissue, are therefore subject to as little radiation as possible and preferably to none at all. The collimator can be a single piece or be made of multiple pieces that are movable such that the distribution of radiation over the field need not be uniform (one region can be given a higher dose than another). The gantry can be rotated so as to allow different beam angles and radiation distributions without having to move the patient. The central treatment processing or control unit 130 is typically located apart from the radiation treatment device 100. The treatment unit 130 includes output devices such as at least one visual display unit or monitor 160 and an input device such as a keyboard 170. Data can be input also through data carriers such as data storage devices or a verification and recording or automatic setup system. The treatment processing unit 180 is typically operated by the therapist who administers actual delivery of radiation treatment as prescribed by an oncologist by using the keyboard 170 or other input device. The therapist enters into the control unit of the treatment unit 130 the data that defines the radiation dose to be delivered to the patient, for example, according to the prescription of the oncologist. The program can also be input via another input device, such as a data storage device. Various data can be displayed before and during the treatment on the screen of the monitor 160. Similar to the gamma ray imager described in FIG. 1, the desired results from the radiation treatment apparatus is in part accomplished by the use of a collimator having a specific design.

FIGS. 1 and 2 merely are two examples of medical applications that utilize collimators. Many other medical devices incorporate the use of collimators. Collimators in these other types of medical devices can be formed by the method of the present invention. As medical technology has progressed, the sophistication of design for the components of these medical devices has significantly increased. With respect to collimators, the specific configurations of the collimators being used in various medical devices has become much more complex in order to achieve more accurate results. In addition, the acceptable error tolerances of manufacture for these collimators has significantly decreased. The present invention addresses the latest technology demands for the manufacture of collimators.

Figure 3:
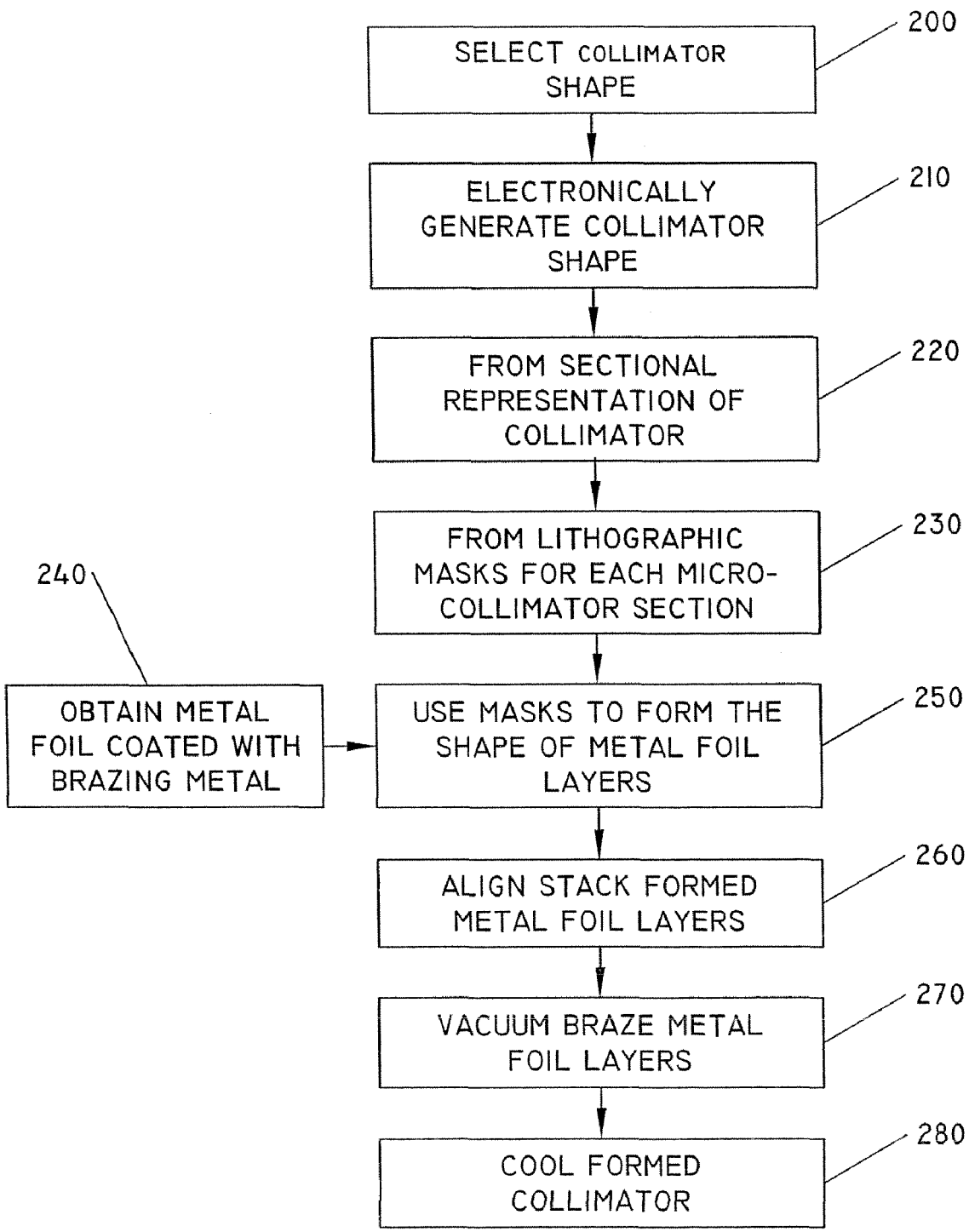
FIG. 3 is a flowchart of an exemplary embodiment of a method of the present invention.

Reference is now made to FIG. 3 which illustrates a flowchart of for manufacturing a collimator in accordance with the present invention. The first step of the manufacturing process 200 is to determine the desired shape of the collimator. Typically the medical device manufacturer will have or provide the particular specifications for the collimator to be used in the medical device. The drawing of the device may be a mechanically drawn device and/or may be an electronically generated device.

Once the desired shape of the collimator is determined, the shape of the collimator needs to be electronically entered 210 so as to form a three dimensional computer generated image of the collimator. One software package that can be used to generate the three dimensional computer generated collimator is AutoCAD. Many other CAD software programs or other types of drawing programs can be used.

After the collimator is electronically entered, the drawing is electronically sectioned or sliced into a plurally of cross-sections 220. The sections or slices of the collimator are taken along a single axis (e.g., longitudinal, vertical, horizontal, etc.). The thickness of each section or slice of the collimator is representative of the thickness of the metal foil to be used to form the collimator. The thickness of the metal foil is typically very thin, thus many sections or slices of the collimator need to be electronically generated. Each of the sections also includes one or more holes or slots that will be used to orient the formed foil layers and also be used to maintain the position of the formed foil layers during heating and cooling of the foil layers. Typically these holes or slots are positioned about the periphery of the each section; however, the holes or slots can be positioned in other locations.

Once the sections or slices of the collimator are generated, a lithographic mask is produced 230 for each section of the collimator. Each lithographic mask defines the features of each unique section of the collimator. The process for producing lithographic masks is well known in the art, thus will not be further described herein.

After the lithographic masks are produced for each section of the collimator, metal foil that is coated with a brazing metal is obtained 240. As can be appreciated, the coated metal foil can be obtained prior to the formation of the lithographic masks. The metal foil that is used to form the collimator typically is a high density material having a specific gravity of at least about 8.5 g/cm³. One metal that can be used is tungsten having a specific gravity of about 19.3 g/cm³. Materials formed of tungsten or other high density materials are typically very difficult to form. Tungsten is a very hard substance and has a extremely high melting point. Consequently, past collimators made of tungsten or other high density metals were very difficult and expensive to manufacture and further resulted in an end product that often did not meet the tolerance requirement necessary for the collimator, thereby resulting in expensive waste. The present invention overcomes this problem. Thin metal foils of tungsten and other high density metals are commonly available. The thickness of the metal foil used in the present invention is generally about 40-150 microns. As can be appreciated, other metal thicknesses can be used. The metal foil is also coated on one or both sides by a brazing metal. The coating of the brazing metal is typically by an eletroplating process; however, other coating processes can be used. The coating thickness of the brazing metal is typically about 0.2-1.5 microns; however, other thicknesses can be used. The brazing metal is typically a high density metal (e.g., at least about 8 g/cm³) having a melting point that is less than the metal that forms the metal foil. When tungsten is used for the metal foil, nickel is typically used as the brazing metal; however, other brazing metals can be used.

Once the coated metal foil is obtained, the metal foil is subjected to lithographic micro-machining techniques and/or micro-machining techniques 250 to produce patterned metal foil layers that are ultimately used to form the collimator. Some of the micromachining techniques that can be used include photo-etching and reactive ion etching.

After the foil layers have been formed, the foil layers are aligned and stacked 250 to form the desired 3-D shape of the collimator. The foil layers should be stacked so that a brazing metal exists between each foil layer. This arrangement can be achieved in a number of different ways. One non-limiting way is to have one side of each of the foil layers coated with the brazing metal. The alignment of the foil layers can also be accomplished in a variety of ways. Typically alignment pins or other fixed structures are used to align the multiple layers of metal foil. The holes or slots in the metal foil are inserted onto the alignment pins thereby properly orienting the foil layers with respect to one another.

The aligned and stacked metal foil layers are then subjected to heat 270 so as to braze together the metal foil layers. The heating of the coated metal foil layer at a proper elevated temperature for a sufficient time will result in the metal coating to melt and flow between the metal layers. Typically, the brazing process is conducted under a vacuum; however, this is not required. The heating of the metal foil layers typically occurs in an inert atmosphere; however, this is not required. During the heating process, the metal foil layers expand. The alignment holes or slots maintain the foil layers in alignment during this heating process. Typically the alignment holes or slots in each foil layer is sized and shaped to account for the expansion of the foil layers during heating. As such, when the foil layers are heated at or near their maximum temperature, wherein the brazing material is partially or fully liquified, the holes or slots line up relative to the alignment pins so as to form the desired shaped of the collimator.

Figure 4:
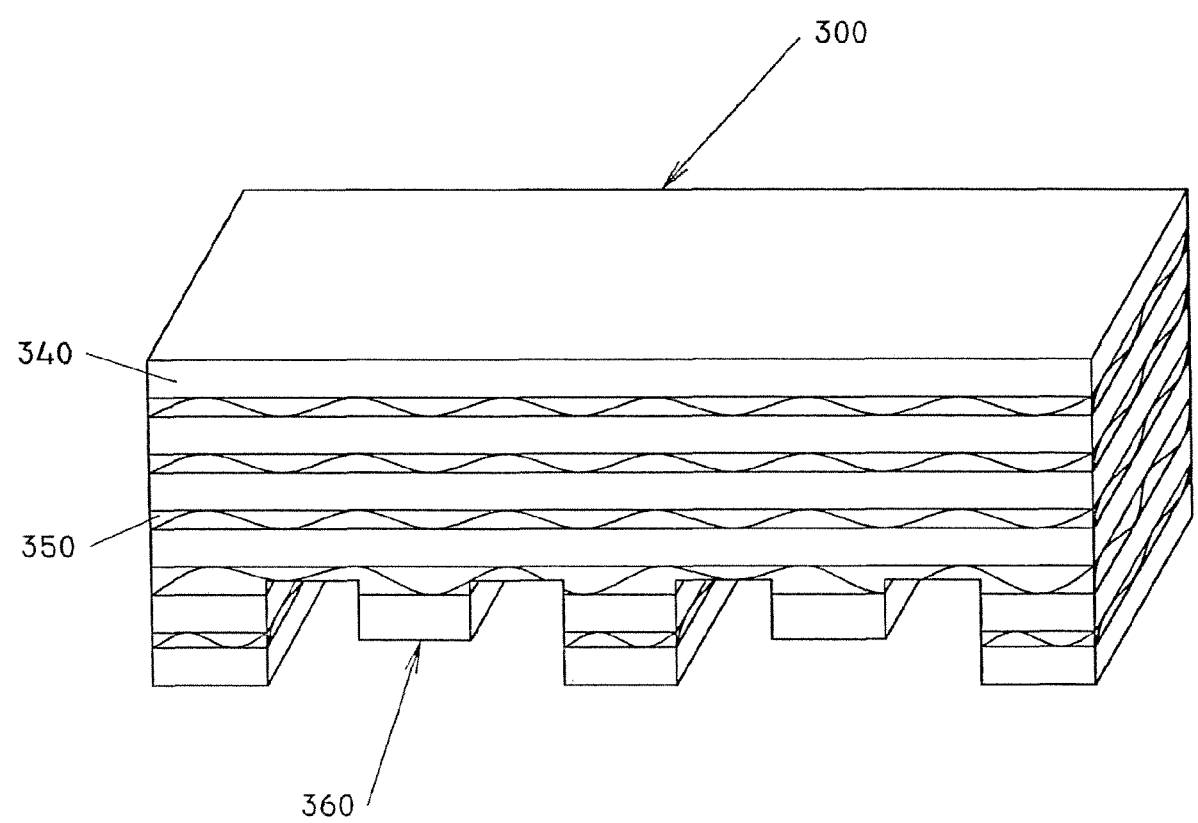
FIG. 4 is a side elevation view of a collimator made by the process illustrated in FIG. 4.
Figure 5A:
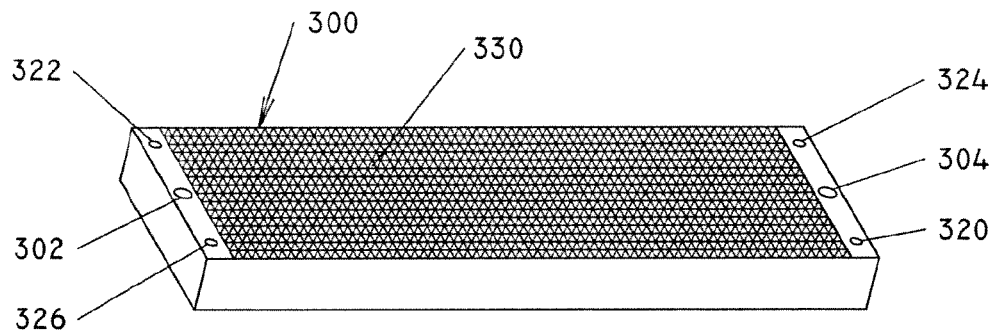
FIG. 5A is a exemplary collimator that can be formed by the method of the present invention; and, FIG. 5B is another exemplary collimator that can be formed by the method of the present invention.
Figure 5B:
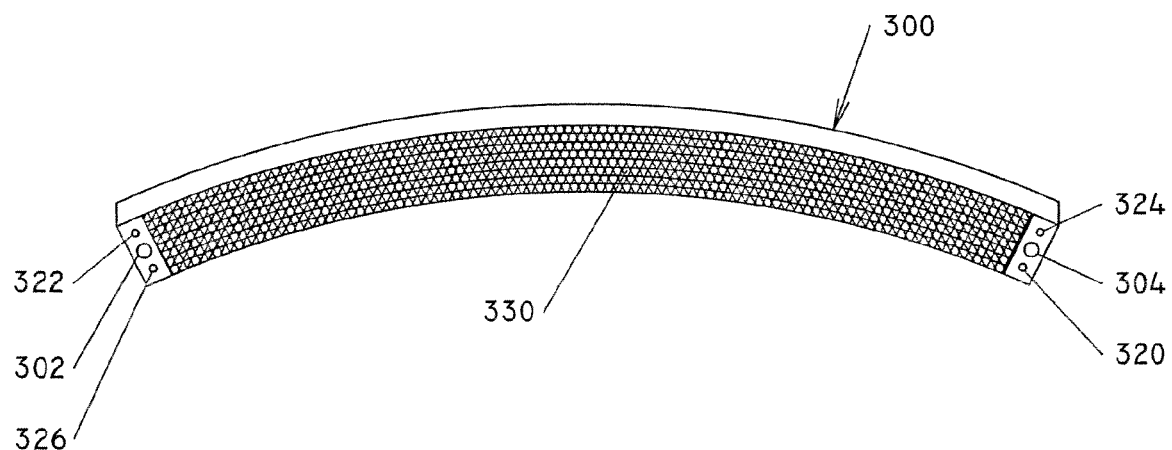

Once the metal foil layers are heated for a sufficient time, the formed collimator is cooled 280. When the foil layers are cooled, the brazing material solidifies thereby locking the foil layers in position relative to one another. The alignment holes or slots in the foil layers are sized and shaped so as to allow the locked together foil layers to contract during cooling. Typically, the cooling occurs in an inert atmosphere; however, this is not required. The use of the above method to manufacture a collimator results in a cost effective process to manufacture high density materials into a variety of shapes within very low error tolerances. FIG. 4 illustrates a section of a collimator that has been formed by the above-described process. Collimator 300 includes a plurality of metal toil layers 340 that are connected together by brazing metal 350. The bottom surface of the collimator has anon-planar surface 360. As can be appreciated, many bottom surface configurations can be formed to be used in a particular application. FIG. 5A illustrates a collimator 300 that can be formed by the present invention. Collimator 300 can be formed in a variety of other shapes and sizes, depending on the desired end use and configuration of the collimator. Collimator 300 is illustrated as being a single component of the whole collimator. Mount holes 302, 304 are used to mount or secure the collimator component on a frame or other structure. Four guide holes 320, 322, 324, 326 are located on the face of the collimator. These guide holes are used to align the foil layers during the formation of the collimator. As can be appreciated, the holes can be used to align and/or mount or secure the collimator to a medical device. The top face of the collimator 330 has a non-flat surface that has been selected for a particular application. As can be appreciated, other surface configurations can be formed. In addition, the surface of the collimator can include slots, grooves, channels, holes, etc. to achieve the desired results from the collimator. As stated above, the collimator 300 is represented as one section of a larger collimator. As can be appreciated, collimator can be formed from a single piece instead of from a plurality of sections. Such a collimator is illustrated in FIG. 5B. In several medical devices the length of the collimator is about 0.5-2 meters long. The method of forming a collimator in accordance with the present invention can be used to form a one piece collimator that has a length of 0.5-2 meters. Heretofore, it is believed that a one piece metal collimator having low error tolerances has not been made. Single piece collimators have advantages over segmented collimators, especially in newer scanner designs. In the newer collimators, the collimator spins around the patient and results in increased vibrations and forces on the collimator. When sectioned collimators are used in such systems, the vibrations and forces on the collimator act on the interlocking slits and cause the slits to wear and break. Single piece collimators overcome this problem. The method of the present invention can form metal foil layers that can be used to form a one piece collimator or a collimator formed from a plurality of sections. Collimator 300 is also illustrated as having a generally planar surface 330. As can be appreciated, the one piece collimator or one or more sections of a collimator can have an arcuate profile or a number of other profiles.

The following example illustrates the manufacture of a collimator in accordance with the present invention. The manufacturing process of the present invention can provide methods for fabricating grid structures having high-resolution and high-aspect ratio, which can be used for radiation collimators, scatter reduction grids, and/or detector array grids. Such devices can be used in the field of radiography to, for example, enhance image contrast and quality by filtering out and absorbing scattered radiation (sometimes referred to as "off-axis" radiation and/or "secondary" radiation). These devices can be used in nearly every type of imaging, including astronomy, land imaging, medical imaging, magnetic resonance imaging, tomography, fluoroscopy, non-destructive inspection, non-destructive testing, optical scanning (e.g., scanning, digital copying, optical printing, optical plate-making, faxing, and so forth), photography, ultra-violet imaging, etc. Thus, these devices can be used in telescopes, satellites, imaging machines, inspection machines, testing machines, scanners, copiers, printers, facsimile machines, cameras, etc. The term "collimator" is used generally to describe a radiation collimator, x-ray grid, scatter reduction grid, detector array grid, or any other grid used in an imaging apparatus and/or process. Certain collimators can be placed between the object and the image receptor to absorb and reduce the effects of scattered x-rays. Moreover, such collimators can be used in a stationary fashion, like those used in SPECT (Single Photon Emission Computed Tomography) imaging, or can be moved in a reciprocating or oscillating motion during the exposure cycle to obscure the grid lines from the image, as is usually done in x-ray imaging systems. Grids that are moved are known as Potter-Bucky grids. X-ray grid configurations can be specified by grid ratio, which can be defined as the ratio of the height of the grid to the distance between the septa. The density, grid ratio, cell configuration, and/or thickness of the structure can have a direct impact on the grid's ability to absorb off-axis radiation and/or on the energy level of the x-rays that the grid can block. The open cells of the ceramic grid structure can be filled with detector materials that can be accurately registered to a collimator. The grids can be fabricated to have high-resolution grid geometries that can be made in parallel or focused configurations. The grid can have very fine septal walls, or can have an air-cell grid structure. The manufacturing process of the present invention can be used to manufacture any collimator configuration desired for a particular application.

The first part of the manufacturing process involves the generation of a three-dimensional computer model of the collimator. The computer generated model of the collimator is divided into a plurality of thin sections that are cut parallel to the longitudinal axis of the collimator. The thickness of the sections is substantially uniform and reflects the thickness of the metal foil to be used to make the collimator. Guide holes or slots are also inserted for each section. The number, size and shape of the guide holes or slots are selected to achieve the proper orientation of the foil layers during the heating and cooling of the foil layers.

The metal foil used to form the collimator has a specific gravity of at least about 10.2 g/cm$^3$, a melting point of at least about 1600° C., and a thickness of about 30-150 microns. One non-limiting metal foil is a metal foil formed of molybdenum, niobium, platinum, tantalum and/or tungsten. The metal foil is coated on one side with a thin metal electroplated layer of a metal having a specific gravity of at least 8.5 g/cm$^3$, a metaling point of less than 1470° C., and a thickness of about 0.1-10 microns. Non-limiting examples of metals for the metal coating include copper, gold, lead, nickel and/or silver. A specific example of a coated metal foil for use in manufacturing a collimator is a tungsten metal foil coated on one side with a electroplated nickel layer wherein the thickness of the tungsten foil is about 77 microns, the thickness of the nickel coating is about 1 micron and the total thickness of the coated metal foil is about 78 microns. In this example, the sliced sections of the computer generated collimator would represent sections having a thickness of about 78 microns. The collimator would thus be formed from about 50-600 layers of metal foil. As can be appreciated, the back or rear portion of the collimator may have a uniform thickness and shape and only the front portion of the collimator has a non-uniform shape. In such circumstances, the metal foil layers can be used to only form the non-uniform portion of the collimator and the uniformly shaped portion of the collimator can be manufactured by a different process (e.g., machining, stamping, molding, etc.). In such an arrangement, the layers of metal foil are later connected to the uniformly shaped portion of the collimator to form the full collimator.

Each of the coated metal foil sheets of nickel coated tungsten were chemically etched to match a specific section of a computer generated section of the collimator. Photo-masks were produced for etching each of the metal foil layers. Each metal foil layer was processed using standard photo-etching techniques and were etched in such a way that the cross-sectional shape of the etched walls for each layer are perpendicular to the top and bottom surfaces of the layer (commonly referred to as straight sidewalls).

Once all the metal foil layers were etched, the metal foil layers were stacked together in order to form the collimator. The guide holes or slots were used to orient the foil layers on graphite guide pins. The metal foil was specifically coated such that a nickel layer existed between each metal foil layer. The stacked metal foil layers were then bonded together by a vacuum brazing process. During the brazing process, the layered assembly was heated in a hydrogen atmosphere to a temperature of 1500-1700° C. for about 20-75 minutes, which caused the coated nickel layer to flow, thereby wetting the surfaces of the tungsten foil layers. The temperature and time of heating was sufficient to allow the nickel to uniformly flow and connect the layers of tungsten foil together at all contact points. The brazed layers of tungsten foil were then cooled in a hydrogen atmosphere for about 1-3 hours and then removed. The formed collimator was removed from the guide pins and then inspected for quality control purposes to determine if the formed collimator fell within accepted tolerances.

While considerable emphasis has been placed herein on preferred embodiments of the invention, it will be appreciated that other embodiments can be devised and that many changes can be made in the preferred embodiments without departing from the principles of the invention. Accordingly, it is to be distinctly understood that the foregoing descriptive matter is to be interpreted merely as illustrative of the invention and not as a limitation.

I claim:

1. A collimator comprising a plurality of metal layers stacked and aligned together to form a bottom surface of said collimator that has a non-planar surface designed to receive and reflect back a source of radiation that is used to generate an image, a plurality of said metal layers formed into specific shapes by use of at least one cutting technique, said specific shapes of a plurality of said metal layers at least partially based on a sectioned computer image of said collimator, a plurality of said metal layers each have an average density of at least about 8.5 g/cm$^3$, a plurality of said metal layers each have an average thickness of less than about 400 microns, a plurality of said metal layers are connected together by brazing.

2. A collimator as defined in claim 1, wherein said cutting technique includes at least one lithographic technique.

3. The collimator as defined in claim 1, wherein a plurality of said metal layers include at least one alignment opening to facilitate in said aligning and stacking of said metal layers prior to connecting said metal layers together by brazing.

4. The collimator as defined in claim 1, wherein a plurality of said metal layers include a brazing metal layer on at least one side of said metal layers, said brazing metal having a melting temperature and average density that is less than said metal layers, said brazing metal having an average density of at least about 8.5 g/cm$^3$, said brazing metal having a different composition from said metal layers, said brazing metal having a melting temperature that is at least 50° C. less than a melting temperature of said metal layers.

5. The collimator as defined in claim 4, wherein said brazing metal layer has an average coating thickness of less than about 10 microns.

6. The collimator as defined in claim 5, wherein said brazing metal has a density of at least about 8.8 g/cm$^3$ and a thickness prior to being brazed heating of at least about 0.5 microns.

7. The collimator as defined in claim 4, wherein said brazing metal includes a metal selected from the group consisting of copper, gold, lead, nickel, platinum, silver, and combinations thereof.

8. The collimator as defined in claim 1, wherein a plurality of said metal layers includes a metal selected from the group consisting of bismuth, cadmium, cobalt, erbium, hafnium, iridium, niobium, osmium, palladium, rhenium, rhodium, ruthenium, tantalum, technetium, terbium, thallium, thulium, tungsten, and combinations thereof.

9. The collimator as defined in claim 7, wherein a plurality of said metal layers include tungsten and a plurality of layers of said brazing metal includes nickel.

10. A collimator comprising a plurality of metal layers stacked and aligned together to form a bottom surface of said collimator that has a non-planar surface designed to receive and reflect back a source of radiation that is used to generate an image, a plurality of said metal layers each have an average density of at least about 8.5 g/cm$^3$, a plurality of said metal layers each have an average thickness of less than about 400 microns, a plurality of said metal layers are connected together by brazing, a plurality of said metal layers include at least one alignment opening to facilitate in said aligning and stacking of said metal layers prior to connecting said metal layers together by brazing, a plurality of said metal layers includes a metal selected from the group consisting of bismuth, cadmium, cobalt, erbium, hafnium, iridium, niobium, osmium, palladium, rhenium, rhodium, ruthenium, tantalum, technetium, terbium, thallium, thulium, tungsten, and combinations thereof.

11. The collimator as defined in claim 10, wherein a plurality of said metal layers include a brazing metal layer on at least one side of said metal layers, said brazing metal having an average density of at least about 8.5 g/cm$^3$, said brazing metal having a different composition from said metal layers, said brazing metal having a melting temperature that is at least 50° C. less than a melting temperature of said metal layers.

12. The collimator as defined in claim 10, wherein a plurality of said metal layers have an average thickness of at least 10 microns.

13. The collimator as defined in claim 11, wherein a plurality of said metal layers have an average thickness of at least 10 microns.

14. The collimator as defined in claim 11, wherein said brazing metal has an average thickness prior to being brazed heating of at least about 0.5 microns.

15. The collimator as defined in claim 13, wherein said brazing metal has an average thickness prior to being brazed heating of at least about 0.5 microns.

16. The collimator as defined in claim 11, wherein said brazing metal includes a metal selected from the group consisting of copper, gold, lead, nickel, platinum, silver, and combinations thereof.

17. The collimator as defined in claim 15, wherein said brazing metal includes a metal selected from the group consisting of copper, gold, lead, nickel, platinum, silver, and combinations thereof.

18. The collimator as defined in claim 11, wherein a plurality of said metal layers include tungsten and a plurality of layers of said brazing metal includes nickel.

19. The collimator as defined in claim 17, wherein a plurality of said metal layers include tungsten and a plurality of layers of said brazing metal includes nickel.

* * * * *